(12) United States Patent
Mu et al.

(10) Patent No.: US 8,224,420 B2
(45) Date of Patent: Jul. 17, 2012

(54) MRI GUIDED ULTRASOUND THERAPY APPARATUS

(75) Inventors: Mu Mu, Chongqing (CN); Wenzhi Chen, Chongqing (CN); Hai Wang, Chongqing (CN); Long Wang, Chongqing (CN)

(73) Assignee: Chongqing Ronghai Medical Ultrasound Industry Ltd., Chongqing (CN)

( * ) Notice: Subject to any disclaimer, the term of this patent is extended or adjusted under 35 U.S.C. 154(b) by 755 days.

(21) Appl. No.: 11/883,096

(22) PCT Filed: Aug. 31, 2005

(86) PCT No.: PCT/CN2005/001366
§ 371 (c)(1),
(2), (4) Date: Apr. 2, 2008

(87) PCT Pub. No.: WO2006/079266
PCT Pub. Date: Aug. 3, 2006

(65) Prior Publication Data
US 2008/0275330 A1   Nov. 6, 2008

(30) Foreign Application Priority Data

Jan. 31, 2005   (CN) .......................... 2005 1 0004984

(51) Int. Cl.
*A61B 5/055*   (2006.01)
(52) U.S. Cl. ........ 600/411; 600/407; 600/410; 600/437; 600/439; 601/2; 601/3; 601/4; 324/309; 324/319
(58) Field of Classification Search ............. 600/407, 600/410, 411, 437, 439; 601/2–4; 324/309, 324/319
See application file for complete search history.

(56) References Cited

U.S. PATENT DOCUMENTS

| | | | |
|---|---|---|---|
| 5,275,165 A | | 1/1994 | Ettinger et al. |
| 5,443,068 A | | 8/1995 | Cline et al. |
| 5,485,839 A | | 1/1996 | Aida et al. |
| 5,526,814 A | | 6/1996 | Cline et al. |
| 5,935,065 A | | 8/1999 | Rose, Jr. et al. |
| 6,128,522 A | * | 10/2000 | Acker et al. ............ 600/411 |
| 6,188,923 B1 | | 2/2001 | Bechtold |

(Continued)

FOREIGN PATENT DOCUMENTS

CN   1215616   5/1999

(Continued)

*Primary Examiner* — Tse Chen
*Assistant Examiner* — Baisakhi Roy
(74) *Attorney, Agent, or Firm* — The Webb Law Firm

(57) ABSTRACT

This invention provides a MRI guided ultrasound therapy apparatus. It comprises a static field magnet adapted to apply a static magnetic field in an magnetic resonance volume at a predetermined disposition; at least one ultrasound energy applicator adapted to apply energy within an energy application zone at a predetermined disposition; and The mechanical positioning means for moving said ultrasound energy applicator to position the applicator so that the energy application zone intersects said magnetic resonance volume within said region of the subject. In that apparatus, the static field magnet is open at both ends or open at side. The sided open is upward or downward and the mechanical positioning means of this ultrasound energy applicator is close to and is located outside of this sided open. This invention reduces the space limitation for the mechanical positioning means of the ultrasound transducer. Meanwhile, the non-magnetic requirement on the mechanical positioning means become less greatly and particularly the problem of interference from magnetic field produced by working current of the transducer power cord to MRI system can be solved.

9 Claims, 2 Drawing Sheets

U.S. PATENT DOCUMENTS

| | | | |
|---|---|---|---|
| 6,208,142 B1* | 3/2001 | Wagshul | 324/319 |
| 6,374,132 B1* | 4/2002 | Acker et al. | 600/411 |
| 6,516,211 B1* | 2/2003 | Acker et al. | 600/411 |
| 6,702,804 B1* | 3/2004 | Ritter et al. | 606/1 |
| 6,773,408 B1* | 8/2004 | Acker et al. | 601/2 |
| 6,794,871 B2* | 9/2004 | Imai et al. | 324/318 |
| 6,845,262 B2* | 1/2005 | Albert et al. | 600/420 |
| 7,264,584 B2* | 9/2007 | Ritter et al. | 600/1 |
| 7,358,726 B2 | 4/2008 | Ochi et al. | |
| 7,771,415 B2* | 8/2010 | Ritter et al. | 606/1 |
| 2002/0123681 A1* | 9/2002 | Zuk et al. | 600/410 |
| 2002/0193681 A1 | 12/2002 | Vitek et al. | |
| 2007/0197953 A1* | 8/2007 | Slade et al. | 604/19 |
| 2010/0301857 A1* | 12/2010 | Hyde et al. | 324/309 |

FOREIGN PATENT DOCUMENTS

| | | |
|---|---|---|
| CN | 1257414 | 6/2000 |
| EP | 0 627 206 | 7/1994 |
| JP | 5-300910 A | 11/1993 |
| JP | 11099139 A | 4/1999 |
| JP | 11313831 | 11/1999 |
| JP | 2003-116812 A | 4/2003 |
| JP | 2003-325510 A | 11/2003 |

* cited by examiner

MRI GUIDED ULTRASOUND THERAPY APPARATUS

FIELD OF THE INVENTION

The present invention pertains to an ultrasound therapy apparatus and more specifically, to a MRI guided high-intensity focused ultrasound (HIFU) therapy apparatus.

BACKGROUND OF THE INVENTION

High-intensity focused ultrasound (HIFU) therapy is a non-invasive and non-traumatic approach. It is particularly applied to the patients with tumors. Comparing to the conventional surgeries or chemotherapy, HIFU therapy brings the patient less trauma and therefore its applications have been developed rapidly. Its indications include liver cancer, bone sarcoma, breast cancer, pancreas cancer, kidney cancer, soft tissue tumor and pelvic tumor.

Most of the existing HIFU therapy use B-mode ultrasound imaging device to locate the region of the subject and to monitor the therapy. Adoption of B-mode ultrasound imaging device has the following advantages: low cost, real time imaging, having the same acoustic path as the therapeutic ultrasound, observing the tissue necrosis after high-intensity focused ultrasound (HIFU) exposures according to gray scale changes of the images. But, B-mode ultrasound image is only a plane image with a certain angle and cannot completely display the relative tissue relationships and solid structure of the region of the subject to be treated, therapeutic acoustic path and the area behind the region of the subject. Even though the 3-D ultrasound system is used, the visible area is still limited. Besides, the ultrasound image is limited on the depth of observation and it almost cannot display the tissue behind the bone because the bone influences the image greatly. The serious noises on the images exist during monitoring treatment. Further, ultrasound images have poor capacity to identify the tissue boundary and particularly it is more difficult to identify small tumors and deep-bedded tumors.

Nuclear Magnetic Resonance Imaging (NMRI) is an important application in biological and medical fields. It has a short name of MRI (Magnetic Resonance Imaging) and also refers to Nuclear Magnetic Resonance• CT (CT is short for computer tomography). The simple principle of MRI is: the patient lies inside an imaging magnet. Radio-frequency signals are then applied to the patient. The hydrogen nuclei in region of the subject are excited by radio-frequency signals and sends weak radio-frequency signals, which refer to nuclear magnetic resonance signals. During this process, the appropriate gradients are applied to the magnetic field so that the magnetic resonance signals can be acquired selectively. The information is processed to gain the tissue characteristics of each point and further the tissue can be imaged.

Magnetic Resonance Imaging (MRI) has great ability to identify different tissue and is easy to distinguish the normal tissue and tumor tissue and to determine the boundary of tumor tissue. MRI provides the volume data of a subject and a part of human body or full body can be imaged, therefore MRI is very suitable for locating the region of the subject to be treated by HIFU and planning HIFU surgical procedures. Meanwhile, with the development of MRI technology, the existing MRI equipment already can gain the images of the tissue in real-time, moreover the image is three-dimensional image with a certain volume. Therefore, MRI provides an excellent technical solution in monitoring the treatment procedures in real-time. Particularly, the temperature image provides a noninvasive temperature measuring method expected by the thermal therapy and has very important significance in controlling HIFU therapeutic dose, treating the region of the subject in time and controlling the energy.

In this art, it has been discovered that the ultrasound therapy for internal tissue of patient is monitored and guided by MRI. In HIFU surgery, MRI may be used to scan the patient for locating the region of the subject to be treated before HIFU treatment and also to guide the ultrasound wave to the region of the subject and monitor the temperature changes of the tissue during HIFU treatment so as to ensure that only the region of the subject is heated without destroying the surrounding normal tissue. The advantages of MRI are well known by the technicians skilled in this art.

At present, the major problem for a MRI guided ultrasound therapy apparatus focus is the interference between a MRI system and a focused ultrasound therapy system. Running of MRI system requires a steady strong magnetic field. In order to ensure the intensity and steadiness of the magnetic field, particularly for a relatively closed magnetic field, when the ultrasound transducer is operated in the magnetic field, the space for its mechanical motion locating means is limited greatly. In the field of this art, for this problem, some patents have already aimed to provide some solutions.

Japanese Patent No. 3322649 discloses a therapy system combined a MRI with an ultrasound therapy equipment. This system employs MRI to determine the location of a tumor firstly, and then the patient is moved out from the magnetic field of MRI and then treated by ultrasound. This kind of treatment needs repeated moving of patient and needs location for many times. The locating system is complex and a long time is needed to make locations. Furthermore, the real-time monitoring and on-line monitoring during the treatment are difficult to be realized.

U.S. Pat. No. 5,275,165 "Magnetic resonance guided ultrasound therapy system with inclined track to move transducers in a small vertical space" provides a MRI surgery system, which facilitates surgery with a focused ultrasound transducer that selectively destroys tissue in a region within a subject. The focused ultrasound transducer focalizes energy at a focal point within the region of tissue to be destroyed. A non-magnetic moving positioning device having a vertical dimension movement small enough to fit easily within the bore of a MRI magnet drives an ultrasound energy applicator in a limited vertical space. The positioning device employs a plurality of hydraulic positioners and an inclined plane to position the ultrasound focal point under the control of an operator. A MRI system employing a temperature sensitive pulse sequence creates an image of the tissue and the region being heated to allow the operator to adjust the position of the ultrasonic transducer so as to direct ultrasonic energy to the appropriate location.

U.S. Pat. No. 5,443,068 "Mechanical positioner for magnetic resonance guided ultrasound therapy" similarly discloses a non-magnetic positioning device of an ultrasound energy applicator, which is operated within the bore of a MRI magnet. The purpose of this invention is to provide a simplified positioner, which is operated within the magnetic filed. And also the interference to the magnetic field of MRI system due to the material of the positioning means is avoided. Other similar patents include U.S. Pat. No. 5,275,165 "Magnetic resonance guided ultrasound therapy system with inclined track to move transducers in a small vertical space" and etc.

The solutions described in the US patents as above mentioned are to place an ultrasound therapy transducer and positioning means within the static magnetic field of MRI system. The positioning means move the therapy transducer and the focal points of the transducer are used to expose the tumor and therefore the treatment on diseases and the monitoring in real-time have been achieved. The means to solve the technical problem is mainly aimed at the non-magnetic designs of therapy transducer and the positioning means and minimizing the volume of the positioning means and the operation space for it as far as possible to meet the working requirements of ultrasound energy applicator within MRI magnetic field. These technical solutions mainly have the following disadvantages: 1) Because the highly required non-magnetic designs and treatment on the therapy transducer and its positioning means, the technical complex and the cost are increased; 2) Because the positioning means are located within the magnetic field, the movement range of ultrasound transducer is limited strictly and furthermore the high-intensity focused ultrasound therapy needs a very precise locating system and the positioning means of the real therapy equipment in clinical applications are usually large, this technical solution increases the difficulties of equipment manufacturing and actual applications; 3) Because one part of the conductor used to supply power to the transducer is located within magnetic field, the magnetic field produced by the working current flow of the conductor will bring a big interference to MRI system, which is sensitive to magnetic signals; 4) It is difficult to perform assistant manual operations for an operator and also it is inconvenient for an operator to make clinical observations.

Chinese Pat. No. 98805359.4 "MRI guided therapeutic equipment and method" discloses a new type of MRI equipment. The static magnetic field (main magnetic field) of this MRI equipment is different from the closed or half-closed static magnetic field adopted by conventional MRI equipments. Its technical core is to provide a superconductive single-sided magnetic field. Therefore it is an open magnetic field in a big scale and it has some advantages for movement of therapeutic equipment and it can solve the problems encountered by the US patents as above mentioned.

But, the technical solutions for designs of this magnetic field still have some unsatisfactory points: 1) Weak magnetic field intensity and uneven magnetic line distribution influences the image quality. Under low field, the time for imaging is long and it is very difficult to realize the real-time imaging and the temperature measuring. The effective magnetic resonance volume, i.e. magnetic field available for magnetic resonance imaging is only several centimeters; 2) Because the more complex superconductive technology is needed to be applied, the complexity of the equipment is high and it is very difficult to put it in practice and it is a long time to be a mature applicable technology for this equipment.

Therefore, it is expected to provide a MRI guided ultrasound therapy system, which has a relatively low cost and is easy to be operated and particularly is suitable for high-intensity focused ultrasound therapy. Thereby, the ultrasound therapy technique can be further improved to enhance the safety and shorten the treatment time.

SUMMARY OF THE INVENTION

Object and Technical Solutions of the Present Invention

One object of the invention is to utilize the existed mature MRI system with a relatively low cost in conjunction with the existing ultrasound therapy equipment. The interference from ultrasound therapy equipment to MRI shall be minimized as far as possible and the ultrasound therapy guided by MRI can be realized.

A further object of the invention is to provide a MRI guided ultrasound therapy apparatus particularly suitable for performing high-intensity focused ultrasound therapy.

Another object of the invention is to use an open flexible container in a MRI guided ultrasound therapy apparatus to couple the ultrasound energy applicator to the patient to be treated so as to further ensure the safety and ideal therapeutic effects of high-intensity focused ultrasound therapy.

After the interference problem due to MRI used in conjunction with a high-intensity focused ultrasound therapy system has been solved, a further object of the invention is to utilize MRI system to obtain the information and relative digitalization processing and accordingly the MRI monitoring in real-time and the ultrasound therapy guided by MRI are realized.

In order to realize the objects of the present invention and to solve the existing technical problems, the invention provides a MRI guided ultrasound therapy apparatus, wherein comprising:

a. A static field magnet adapted to apply a static magnetic field in an magnetic resonance volume at a predetermined disposition;

b. At least one ultrasound energy applicator adapted to apply energy within an energy application zone at a predetermined disposition; and c. The mechanical positioning means for moving said ultrasound energy applicator to position the applicator so that the energy application zone intersects said magnetic resonance volume within said region of the subject.

In that apparatus, the static field magnet is open at both ends or open at side. The sided open is upward or downward and the mechanical positioning means of this ultrasound energy applicator is close to and is located outside of the sided open.

The open magnet adopted by this invention has many options in the existing technology. The magnet may be C-shaped one or U-shaped one. The permanent magnet with magnetic field intensity of over 03 T is preferred. Additionally, the existing superconductive open magnet is also preferred and it can provide face-to-face magnetic fields. It has two ends and one open at side. The magnetic field intensity is over 0.5 T.

During treatment, the patient is fixed and positioned in the magnetic gap of a static field magnet. If the magnetic gap is open upward, the ultrasound energy applicator may be placed above that open. If the magnetic gap is open downward, the ultrasound energy applicator may be placed under that open. In order to further reduce electromagnetic interference, the ultrasound energy applicator may be placed beyond the side open of the static field magnet.

The present invention adopts the magnetic gap with an upward or downward open because most of high-intensity focused ultrasound therapy apparatuses need the fluid coupling agent. The container for the fluid coupling agent had better be made of flexible material. The container shall fully and closely contact with the body of the subject to be treated so that the unexpected ultrasound waves reflection surface can be avoided. Thus, technically if the ultrasound energy applicator is located at an upper position, the subject to be treated is positioned within the bore of magnet with an upward open or if the ultrasound energy applicator is located at a lower position, the subject to be treated is positioned within the bore of magnet with an downward open. In this way, the MRI guided treatment can be implemented easily and it is particularly suitable for high-intensity focused ultrasound therapy apparatus.

Further, for the apparatus as above mentioned, the downward open of magnetic gap is preferred. A treatment bed can be used to move and fix the subject to be treated. The bed has a rectangle open or a circular one, which is used to accommodate the coupling agent container of ultrasound therapy apparatus. In this technical solution, an open flexible fluid container can be adopted so that the patient can directly contact with the fluid in the container. Accordingly the patient is coupled to the ultrasound energy applicator of the ultrasound therapy apparatus by the coupling agent in the container. Thus, the acoustic membrane between the skin and container can be left out and the heat radiation becomes easier and the acoustic energy deposition at the skin surface in the acoustic path can be reduced. The coupling agent in the container is degassed water.

When the static field magnet has an upward open at side, the flexible fluid container is closed by flexible acoustic membrane and this membrane is used as the contacting surface with the patient. Also, the closed side of the magnet can be used as the bed to fix the patient.

This invention improves the interference problem between MRI system and ultrasound therapy apparatus. MRI images may be used to locate the region of the subject to be treated, check ultrasound beam transmission path and make treatment procedures.

This invention also provides a therapy apparatus, which uses the real-time MRI fast images to monitor the acoustic energy application to the region of the subject to be treated and/or check ultrasound beam transmission path.

The apparatus provided by this invention further includes a receiving and processing means to obtain the local temperature information on the region of the subject to be treated and/or ultrasound beams transmission path within the magnetic resonance volume from MRI system.

Further, this invention provides a MRI guided ultrasound therapy apparatus. The ultrasound energy applicator is located outside of the open at side of the static field magnet. Thus, the interference to MRI magnetic field may be reduced further and more accurate images can be ensured.

Lastly, this invention provides a magnetic resonance apparatus. Its static field magnet is an open magnet with opens at both ends and at one side of the section, and the open of the section of the open magnet directs upward or downward and the downward open of the section is preferred. Further, the permanent magnet is adopted preferably as the static field magnet. The disposition of static field magnet with such upward or downward open has not been disclosed in the existing magnetic resonance apparatuses. It is particularly suitable to use in conjunction with high-intensity focused ultrasound therapy apparatus so as to realize the real-time monitoring treatment or on-line treatment.

BENEFICIAL EFFECTS OF THIS INVENTION

Aiming at the conditions that the existing technologies mostly adopted the non-magnetic designs and operations within magnetic field, this invention is to adopt the existing open magnetic field and put the mechanical positioning means of the ultrasound transducer outside of the main magnetic field and reduce the space limitation for the mechanical positioning means of the ultrasound transducer. Meanwhile, the non-magnetic requirement on the mechanical positioning means become less greatly and particularly the problem of interference from magnetic field produced by working current of the transducer power cord to MRI system can be solved. Further, also the ultrasound transducer may be located outside of the main magnetic field. Thus, the interference of magnetic field produced by the power used by ultrasound therapy equipment to MRI system can be reduced further and the problem of interference from magnetic field produced by working current of the transducer power cord and the positioning means in US patents as above mentioned to MRI magnetic field has been be solved. Meanwhile, with this invention, the medical personnel may change and fix body position of a patient, monitor and operate a patient to some extent.

The existing high-intensity focused ultrasound therapy apparatus can be easily reconstructed and adopted by this invention.

With the development of MRI technology, more and more kinds of open magnetic fields can be selected. A lot of magnetic material is produced in north of China and the level of general techniques of permanent magnet open MRI system in China has reached the world advanced level. If the advantageous MRI technology in China is selected and used in conjunction with ultrasound therapy technology, the application cost can be decreased greatly and it has a good market expectation.

This invention may expand the application range of the conventional high-intensity focused ultrasound therapy. It is especially suitable for relatively complex tumor treatment and has good social benefits. Especially, the arrangement of MRI system in this invention is adaptive to the technical solutions disclosed in Chinese Patent No. 98100283.8 "High intensity focused ultrasound system for scanning and curing tumor" submitted before by the inventor of this invention and the ultrasound therapy system with an open flexible fluid container can be selected by this invention. Accordingly the safety and good effects of high-intensity focused ultrasound therapy can be ensured.

This invention may mostly or fully maintain the examining area in MRI (Magnetic Resonance Imaging) apparatus, but Chinese Patent No. 98805359.4 "MRI-guided therapeutic unit and methods" is very difficult to achieve this. The large examining area makes clinical observations more visual and convenient. MRI system may reserve many functions so as to promote its compatibility and availability ratio.

BRIEF DESCRIPTION OF THE DRAWINGS

The above paragraphs have summarized this invention. Thereinafter, the invention is further described in detail by the preferred embodiments set forth below, taken in conjunction with the accompanying drawings, so that the technicians skilled in this art can understand the implementation of the invention easier and the objects and advantages of the present invention would be more readily apparent.

DETAILED DESCRIPTION OF THE PREFERRED EMBODIMENTS

The ultrasound energy applicator of the present invention specifically refers to a focused ultrasound transducer. This transducer may be a single circular piezoelectric ceramic plus acoustic lens for focusing, or a single sphere piezoelectric ceramic. Also, multiple piezoelectric ceramic cells with same sizes or different sizes may be combined to form a sphere transducer. The transducer may be driven by a single signal or multiple signals according to phased controls. Also, the transducer may vary the parameters, such as shape of surface, area, focal length, frequency, shape of focus and etc. according to different treatment positions.

Embodiment 1

Figure 1:
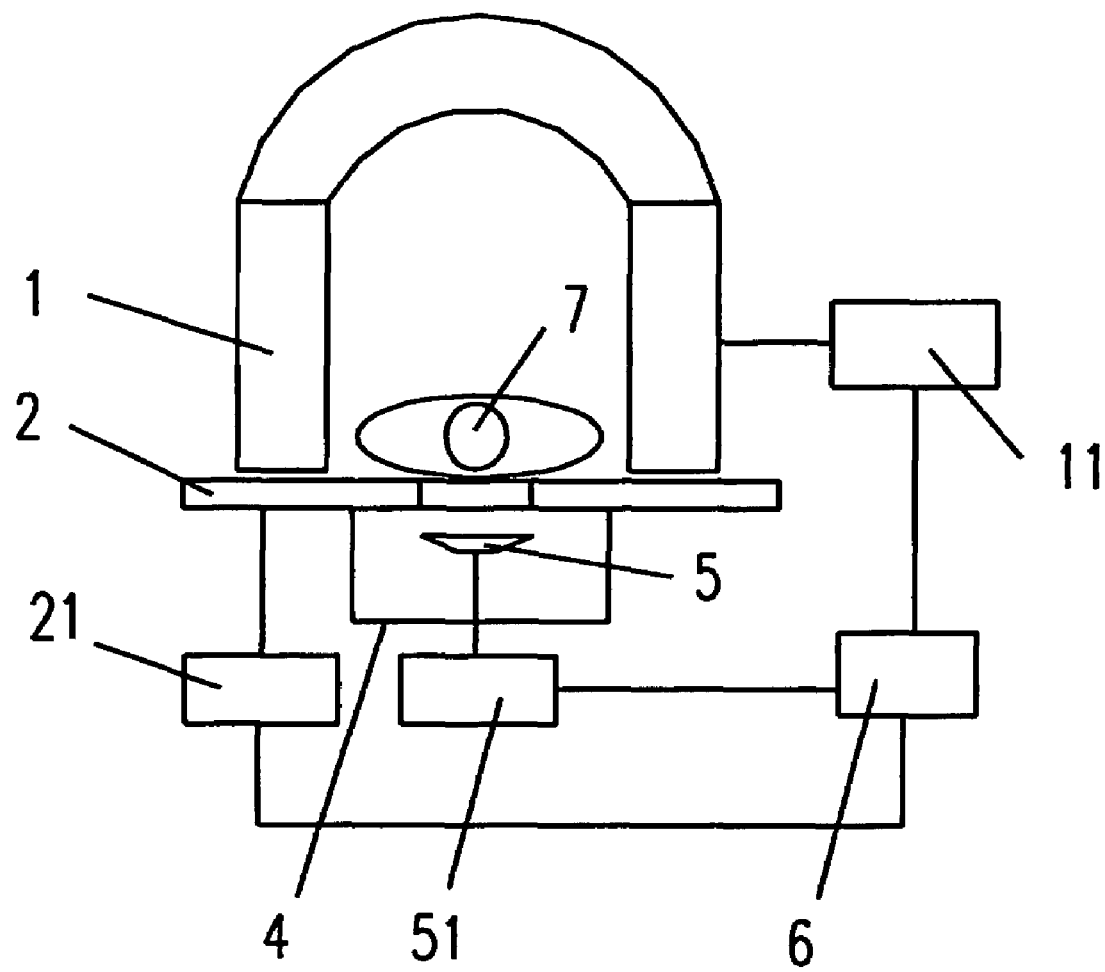
FIG. 1 is a diagrammatic view depicting system structures arrangements in accordance with one embodiment of the invention.

The system illustrated in FIG. 1 comprises magnet 1, treatment bed 2, water container 4, therapy transducer 5, control system 6, MRI image processing means 11, mechanical positioning means for treatment bed 21, mechanical positioning means for therapy transducer 51 and patient to be treated 7 located within the system. The magnet 1 is a 0.3 T permanent magnet (For example, 0.3 T NMR permanent magnet produced by Ningbo Heli Magnetech Co. Ltd.) with an downward open. The gradient field unit is used to code x\y\z three-dimensional space of the magnetic field. RF unit sends imaging sequence signals and receives the magnetic resonance response signals from the body and the MRI image processing means 11 rebuilds the tissue structural image and temperature image.

Therapy transducer 5 is a sphere-focusing piezoelectric transducer with a focal length of 100 mm-150 mm, a diameter of 120 mm-150 mm and a working frequency from 0.5 Mhz to 2 MHz. The therapy transducer 5 is connected to the mechanical positioning means for therapy transducer 51. Driving by that mechanical positioning means, the therapy transducer 5 can move along x, y, z-axis with a moving range of ±100 mm and rotate around x\y\z-axis about ±45 degrees.

The ultrasound wave medium between the ultrasound therapy transducer 5 and the body of patient to be treated 7 is the degassed and deionized purified water with a controlled temperature of about 25 degrees centigrade.

The treatment bed 2 is located outside of the open of the magnet 1 and the material for that bed is non-magnetic material in order to reduce the interference to the magnetic field as far as possible. A hole is located in the middle of the treatment bed 2 so as to transmit the therapeutic ultrasound waves and the water container 4 is connected under the hole. The treatment bed 2 is supported by mechanical positioning means for the treatment bed 21. The mechanical positioning means 21 drive the treatment bed 2 to move horizontally along the axis direction of patient body in a moving range of ±200 mm and move vertically in a moving range of ±200 mm.

The MRI image processing means 11, the mechanical positioning means for the treatment bed 21 and the mechanical positioning means for therapy transducer 51 are connected to the control system 6. The control system 6 drives the mechanical positioning means for treatment bed 21 moves the treatment bed 2 and lets the diseased part of the patient to be treated 7 locate within the magnetic resonance volume, then the MRI image processing means 11 image the diseased part. The control system 6 drives the mechanical positioning means for therapy transducer 51 to let the focal point of the therapy transducer 5 and the diseased part of the region of the subject are overlapped within the magnetic resonance volume, then the therapeutic ultrasound beams are emitted to treat the patient.

In this embodiment, the treatment bed 2, the water container 4, the therapy transducer 5, the control system 6, the mechanical positioning means for treatment bed 21 and the mechanical positioning means for therapy transducer 51 are located outside of the magnet so as to avoid big interference to the magnetic field.

Embodiment 2

Figure 2:
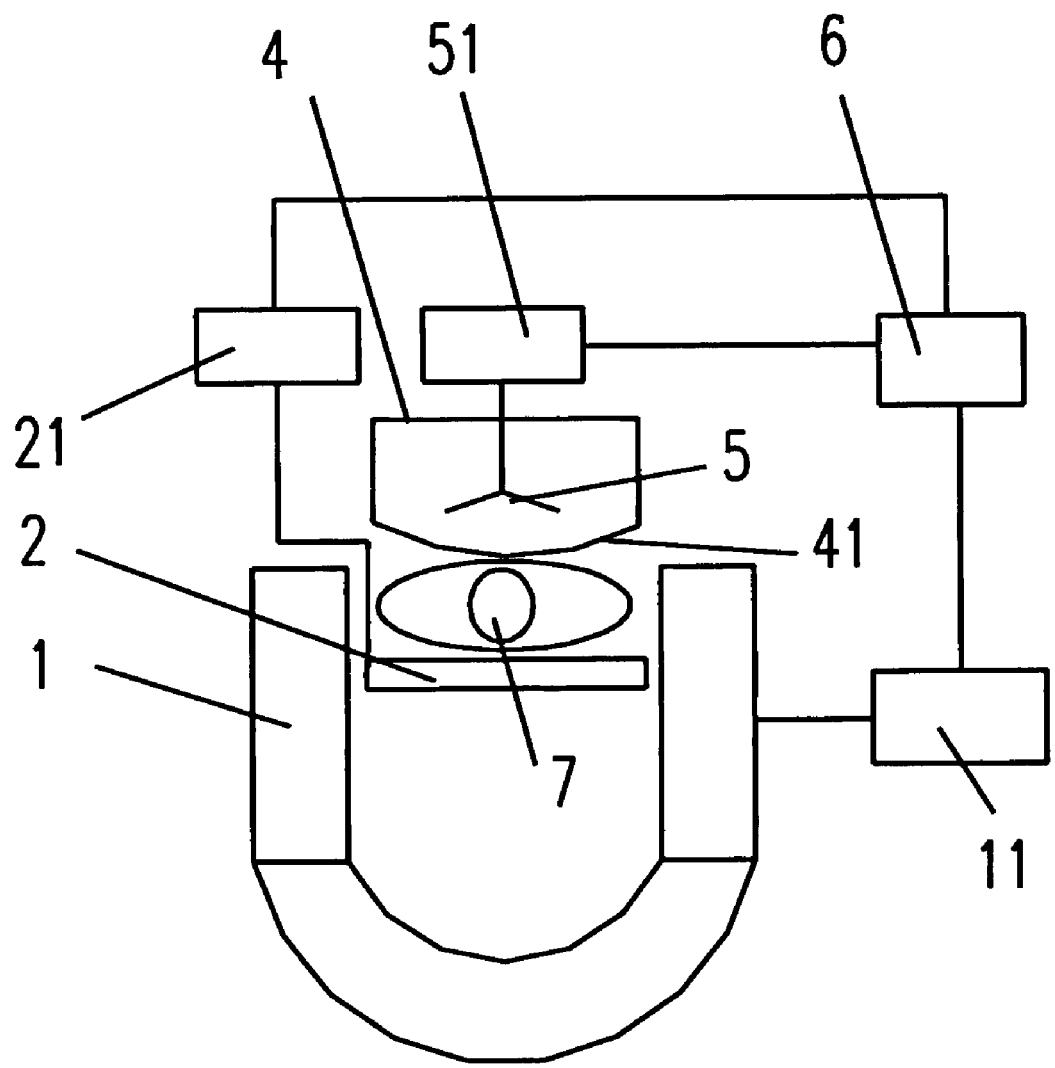
FIG. 2 is a diagrammatic view depicting system structures arrangements in accordance with another embodiment of the invention.

The system illustrated in FIG. 2 comprises magnet 1, treatment bed 2, water container 4, therapy transducer 5, control system 6, MRI image processing means 11, acoustic membrane 41, mechanical positioning means for treatment bed 21, mechanical positioning means for therapy transducer 51 and patient to be treated 7 located within the system. Magnet 1 of the system is a 0.3 T permanent magnet (For example, 0.3 T NMR permanent magnet produced by Ningbo Heli Magnetech Co. Ltd.) with an downward open.

The treatment bed 2 is located within the gap of the magnet 1 and supports the patient to be treated 7. The water container 4 and the therapy transducer 5 are mounted on the mechanical positioning means for therapy transducer 51. There is the acoustic membrane 41 at the surface of the water container 4. This membrane may prevent the medium water from overflowing.

In this embodiment, the ultrasound therapy is applied to a patient from up to down. Other components and their functions in this embodiment are the same as those in embodiment 1 and therefore they are not repeated here.

The technicians skilled in the art may easily make numerous changes and modifications of the embodiments described as above or make it apply to other fields. This invention includes all kinds of embodiments and applications. Even through this invention is described according to the preferred embodiments, therefore the scope of the invention is not to be restricted, except by the following claims of this invention.

THE LIST OF MARKING NUMBERS IN THE DRAWINGS

1 Magnet
2 Treatment bed
4 Water container
5 Therapy transducer
6 Control system
7 Patient to be treated
11 MRI image processing means
21 Mechanical positioning means for treatment bed
41 Acoustic membrane
51 Mechanical positioning means for therapy transducer

The invention claimed is:

1. An MRI guided high-intensity focused ultrasound therapy apparatus, comprising,
    a) a static field magnet adapted to apply a static magnetic field in a magnetic resonance volume at a predetermined disposition;
    b) at least one ultrasound energy applicator adapted to apply energy within an energy application zone at a predetermined disposition; and
    c) a mechanical positioning means for moving said ultrasound energy applicator to position the applicator so that the energy application zone intersects said magnetic resonance volume within a region of a patient to be treated,
    wherein said static field magnet is open at both ends and open at one side, and, during treatment, the patient to be treated is fixed and positioned in a magnetic gap of the static field magnet,
    the open at side is either upward or downward, and the mechanical positioning means of said ultrasound energy applicator is close to and outside of said open at side, and said ultrasound energy applicator is also located outside of the open at side.

2. The apparatus as claimed in claim 1, when said static field magnet has a downward open side, further comprises an open flexible fluid container, which makes said patient to be treated contact said fluid directly.

3. The apparatus as claimed in claim 2, further comprising a treatment bed for fixing said patient to be treated, said treatment bed has an open side, and said flexible fluid container couples to the patient through this open side, wherein said fluid is degassed water.

4. The apparatus as claimed in claim 3 wherein, when said static field magnet has an upward open side, said flexible fluid container is closed by a flexible acoustic membrane and the flexible acoustic membrane is used as a contacting surface with the patient.

5. The apparatus as claimed in claim 4, wherein the closed side of said magnet may be used as a treatment bed for fixing the patient.

6. The apparatus as claimed in claim 1, wherein an MRI image is used to locate the region of the patient to be treated, check ultrasound beams transmission path and make treatment procedures.

7. The apparatus as claimed in claim 1, wherein a real-time MRI fast image is used to monitor acoustic energy application to the region of the patient to be treated and/or check an ultrasound beam transmission path.

8. The apparatus as claimed in claim 1, further comprising a receiving and processing means to obtain local temperature information on the region of the patient to be treated and/or an ultrasound beams transmission path within the magnetic resonance volume from an MRI system.

9. The apparatus as claimed in claim 8, wherein the temperature images are used for monitoring treatment.

* * * * *